(12) United States Patent
Van Waes et al.

(10) Patent No.: US 10,829,442 B2
(45) Date of Patent: Nov. 10, 2020

(54) PROCESS FOR THE PREPARATION OF CARBAMATES

(71) Applicant: Taminco BVBA, Ghent (BE)

(72) Inventors: Frederik Van Waes, Bassevelde (BE); Kristof Moonen, Hamme (BE); Dieter Ulrichts, Sint-Adries (BE)

(73) Assignee: Taminco BVBA, Ghent (BE)

( * ) Notice: Subject to any disclaimer, the term of this patent is extended or adjusted under 35 U.S.C. 154(b) by 0 days.

(21) Appl. No.: 16/321,543

(22) PCT Filed: Aug. 3, 2017

(86) PCT No.: PCT/EP2017/069659
§ 371 (c)(1),
(2) Date: Jan. 29, 2019

(87) PCT Pub. No.: WO2018/024828
PCT Pub. Date: Feb. 8, 2018

(65) Prior Publication Data
US 2019/0169115 A1  Jun. 6, 2019

(30) Foreign Application Priority Data
Aug. 4, 2016 (EP) ..................................... 16182859

(51) Int. Cl.
*C07C 269/04* (2006.01)
*B01J 27/13* (2006.01)
*C07C 271/20* (2006.01)

(52) U.S. Cl.
CPC ............ *C07C 269/04* (2013.01); *B01J 27/13* (2013.01); *C07C 271/20* (2013.01)

(58) Field of Classification Search
None
See application file for complete search history.

(56) References Cited

U.S. PATENT DOCUMENTS

| 3,649,674 | A | * | 3/1972 | Hoyer | A01N 47/12 |
| | | | | | 560/159 |
| 4,621,149 | A | * | 11/1986 | Fukuoka | C07C 271/06 |
| | | | | | 544/172 |
| 5,194,660 | A | | 3/1993 | Leung et al. | |
| 5,962,721 | A | | 10/1999 | Kim et al. | |

FOREIGN PATENT DOCUMENTS

| EP | 0 393 789 A1 | 10/1990 |
| EP | 1 370 141 B1 | 1/2005 |
| EP | 2 338 341 B1 | 7/2013 |
| GB | 1243519 A | 8/1971 |
| WO | WO 01/47871 A2 | 7/2001 |

OTHER PUBLICATIONS

IUPAC definition for "salt", downloaded from http://goldbook.iupac.org/terms/view/S05447 on Jan. 27, 2020 (Year: 2020).*
Notification of Transmittal of the International Search Report and the Written Opinion of the International Searching Authority dated Oct. 9, 2017 for International Application No. PCT/EP2017/069659.
Matzner et al.; "The Chemistry of Chloroformates;" Chemical Reviews; 1964; vol. 64; Issue 4; pp. 645-687.

* cited by examiner

*Primary Examiner* — Amy C Bonaparte
(74) *Attorney, Agent, or Firm* — Kenrick L. Vidale

(57) ABSTRACT

A process for the preparation of N-(dialkylaminoalkyl)-carbamic acid esters, in particular (propyl N-[3-(dimethylamino)propyl] carbamate) comprising an oxidative carbonylation reaction of a compound of general structure (II)

(II)

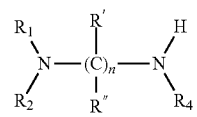

wherein each of $R_1$ and $R_2$, equal to or different from each other, are independently selected from an alkyl group having 1 to 10 carbon atoms, which is optionally substituted by at least one halogen atom, an aryl group or an aralkyl group; $R_3$ is selected from an alkyl group having 1 to 36 carbon atoms, which is optionally substituted by at least one halogen atom, an aryl group or an aralkyl group; each of R', R" and $R_4$, equal to or different from each other, are independently selected from H, an alkyl group having 1 to 10 carbon atoms, which is optionally substituted by at least one halogen atom, an aryl group or an aralkyl group; and n is an integer in the range from 1 to 8, with a hydroxyl compound of general formula (III), $R_3$—OH (III) and in the presence of a catalyst system.

16 Claims, No Drawings

PROCESS FOR THE PREPARATION OF CARBAMATES

CROSS REFERENCE TO RELATED APPLICATIONS

This application is the national stage filing under 35 U.S.C. § 371 of PCT/EP2017/069659, filed Aug. 3, 2017, which claims priority to EP Application EP 16182859.5 filed Aug. 4, 2016, the contents of which are incorporated herein by reference in their entirety.

FIELD OF INVENTION

The present invention relates to a process for the preparation of N-(dialkylaminoalkyl)-carbamic acid esters, in particular (propyl N-[3-(dimethylamino)propyl] carbamate), and their use thereof.

BACKGROUND OF THE INVENTION

Propamocarb, a compound having as IUPAC name propyl N-[3-(dimethylamino)propyl] carbamate, is known to be used in pesticide compositions.

EP 2 338 341 B1, for example, discloses the use of propamocarb-hydrochloride in a pesticide composition comprising further rynaxapyr for protecting plants, crops or seeds against fungal diseases or insect damages. EP 1 370 141 B1 discloses a fungicidal composition comprising propamocarb and a pyridylmethylbenzylamide derivate for the protection of crops against fungal diseases.

The fungicidal and fungistatic action of the salts of N-(dialkylaminoalkyl)-carbamic acid esters, including propamocarb, was for the first time disclosed in GB 1243519. Said carbamic acid esters were described as being suitable for combating the pathogen *Pythium ultimum*.

GB 1243519 further discloses a process for manufacturing the salts of N-(dialkylaminoalkyl)-carbamic acid esters or N-(dialkylaminoalkyl)-thio-carbamic acid esters, in particular propamocarb, with any inorganic or organic acid. Hydrochloric acid and sulphuric acid are acids that are mentioned by way of example to derive said salts of carbamic acid esters. The salts may be manufactured by reacting a dialkylaminoalkylamine with a chloroformic acid ester or thioester, of the general formula

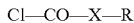

wherein R represents an aliphatic hydrocarbon group containing 2 to 4 carbon atoms, and X represents an oxygen or sulphur atom. Upon reaction, said salt of N-(dialkylaminoalkyl)-carbamic acid ester or N-(dialkylaminoalkyl)-thio-carbamic acid ester is formed.

Thus, the acid, in particular hydrochloric acid (HCl), formed during the reaction pathway associates with the N-(dialkylaminoalkyl)-carbamic acid ester or N-(dialkylaminoalkyl)-thio-carbamic acid ester. In order to obtain the free N-(dialkylaminoalkyl)-carbamic acid ester or N-(dialkylaminoalkyl)-thio-carbamic acid ester, an additional step is necessary to remove the acid, in particular HCl.

Moreover, for the synthesis of chloroformic acid esters or thioesters, of the general formula Cl—CO—X—R, as described above, three major reaction pathways can be distinguished as notably described in Matzner, M. et al. Chemical Reviews, Volume 64, Issue 4, pp 645-687. Namely, chloroformates can be prepared by the reaction of alcohols with phosgene, diphosgene, or triphosgene, by chlorination of alkylformates; or alternatively by the reaction of dialkyl and cyclic carbonates with $PCl_5$. All these synthesis reactions are characterized by having a very low atom efficiency resulting in the formation of a large amount of undesired byproducts.

In view of the above, there is thus a need for an improved process for the preparation of N-(dialkylaminoalkyl)-carbamic acid esters, more in particular for the preparation of propamocarb, having a high overall atom efficiency. Specifically, there is a need for a more environmentally friendly process which is substantially avoiding the production of harmful by-products, and for an economically practical process whereby easily available starting materials can be used, while maintaining a high yield and high purity of the N-(dialkylaminoalkyl)-carbamic acid esters.

SUMMARY OF THE INVENTION

The inventors have now surprisingly found that it is possible to provide an improved process fulfilling the above mentioned needs.

It is thus an object of the present invention to provide a process for the preparation of a compound of general structure (I)

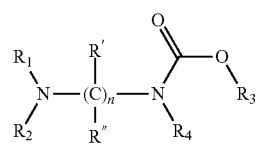

wherein
each of $R_1$ and $R_2$, equal to or different from each other, are independently selected from an alkyl group having 1 to 10 carbon atoms, which is optionally substituted by at least one halogen atom, an aryl group or an aralkyl group;
$R_3$ is selected from an alkyl group having 1 to 36 carbon atoms, which is optionally substituted by at least one halogen atom, an aryl group or an aralkyl group;
each of R', R" and $R_4$, equal to or different from each other, are independently selected from H, an alkyl group having 1 to 10 carbon atoms, which is optionally substituted by at least one halogen atom, an aryl group or an aralkyl group;
n is an integer in the range from 1 to 8,
which comprises an oxidative carbonylation reaction of a compound of general structure (II)

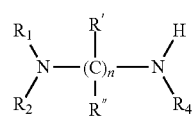

wherein $R_1$, $R_2$, $R_4$, R', R" and n have the same meaning as defined here above,
with a hydroxyl compound of general formula (III), $R_3$—OH (III), wherein $R_3$ has the same meaning as defined here above, and in the presence of a catalyst system, wherein said catalyst system comprises at least one catalyst of the formula $X_kY_l$ [compound $(X_kY_l)$] wherein X is Cu or a metal selected from metals from the Group VIIIB, Y is a halogen, a salt of an organic acid or a salt of an organic compound; and wherein k is an integer 1, 2, 3 or 4 and l is an integer 0, 1, 2, 3 or 4;

at least one halogen containing promoter effective to promote said reaction.

DETAILED DESCRIPTION OF THE INVENTION

For the purpose of the invention, the term "oxidative carbonylation" refers to a process in which a carbon monoxide (CO) is inserted into an organic compound in the presence of an oxidizing agent and a catalyst system.

Oxidative carbonylation of primary, secondary amines and polyamines is known in the art.

For example, WO 01/47871 A2 describes the oxidative carbonylation of aromatic polyamino compounds to polycarbamates. Any aromatic polyamine, in particular polymeric diamino diphenyl methane is reacted with carbon monoxide, an oxidizing agent and an organic hydroxyl compound in the presence of a catalyst system comprising a Group VIII or lanthanide metal and at least one halogen containing promoter.

U.S. Pat. No. 5,962,721 discloses a method for preparing carbamates by reacting a primary or a secondary amine, such as notably linear or branched amine (e.g. methyl amine, ethyl amine, isopropyl amine, butyl amine, isobutyl amine, hexyl amine, dodecyl amine, hexadecyl amine, octadecyl amine, etc.), aromatic amine (e.g. benzyl amine, phenylamine), cycloalkyl amine (e.g. cyclobutyl amine, cyclohexyl amine), and amine compounds having more than one amine group (e.g. 1,4-cyclohexandiamine, cycloalkyldiamine) with an alcohol and a gaseous mixture of CO and $O_2$ in the presence of a copper catalyst.

U.S. Pat. No. 5,194,660 discloses a process for producing a carbamate by reacting a primary or secondary amine compound with CO, at least one organic hydroxyl compound and at least one oxygen-containing oxidizing agent in the presence of a catalyst composition comprising a metal macrocyclic complex.

None of the aforementioned documents discloses the reaction of a primary or secondary amine group with carbon monoxide, at least one organic hydroxyl compound and at least one oxidizing agent in the presence of a catalyst system whereby said primary or secondary amine group is in the vicinity of a bulky tertiary amine group.

The Inventors have now surprisingly found that the compounds of general structure (II) which are characterized by having at least one bulky tertiary amine group, in particular the $-NR_1R_2$ group, as detailed above, in the vicinity of at least one primary or secondary amine group (i.e. $-NHR_4$ group, as detailed above) can successfully undergo an oxidative carbonylation with the hydroxyl compound of general formula (III) $R_3-OH$ (III), as detailed above, in the presence of the catalyst system, as detailed above.

Without being bound to this theory, it appears that when the primary/secondary and tertiary amine groups are present in the same molecule, the bulky tertiary amine group, assists in the oxidative carbonylation reaction of the primary or secondary amine group. As described in detail in the examples below, it is clear that the bulky tertiary amine of the compounds of general structure (II) has a substantial effect on the oxidative carbonylation reaction of the same. If an oxidative carbonylation of a primary/secondary amine group is carried out in the presence of another compound having a tertiary amine group (i.e. not present in the same molecule), the reaction doesn't proceed at all well. Hence it is surprising that the reaction proceeds smoothly if the primary/secondary and tertiary amine group are present in the same molecule.

For the purpose of the invention, the term "aryl group" refers to an aromatic ring group such as notably phenyl and naphtyl, and phenyl and naphtyl substituted by at least 1 halogen atom.

For the purpose of the invention, the term "aralkyl group" refers to an aromatic ring group substituted with alkyl groups such as notably tolyl, biphenylyl, etc.

In a preferred embodiment of the process according to the present invention, $R_1$ and $R_2$ in the compound of general structure (II), equal to or different from each other, are often independently selected from a linear or branched alkyl group having 1 to 8 carbon atoms, which is optionally substituted by at least one halogen atom, an aryl group, for example phenyl, or an aralkyl group. More preferably, $R_1$ and $R_2$ in the compound of general structure (II), equal to or different from each other, are a linear or branched alkyl group having 1 to 5 carbon atoms, being optionally substituted by at least one halogen atom, even more preferably, $R_1$ and $R_2$ in the compound of general structure (II), equal to or different from each other, are methyl, ethyl, n-propyl or isopropyl each optionally substituted by at least one halogen atom.

In a more preferred embodiment of the process according to the present invention, $R_1$ and $R_2$ in the compound of general structure (II) are independently from each other methyl or ethyl, most preferably, $R_1$ and $R_2$ in the compound of general structure (II) are both methyl groups.

In a preferred embodiment of the process according to the present invention, R', R" and $R_4$, equal to or different from each other, are often independently selected from H, a linear or branched alkyl group having 1 to 8 carbon atoms, which is optionally substituted by at least one halogen atom, an aryl group, for example phenyl, or an aralkyl group. More preferably, R', R" and $R_4$, equal to or different from each other, are H, a linear or branched alkyl group having 1 to 6 carbon atoms, being optionally substituted by at least one halogen atom, even more preferably, R', R" and $R_4$, equal to or different from each other, are H or a linear or branched alkyl group having 1 to 4 carbon atoms being optionally substituted by at least one halogen atom, and particularly preferably R', R" and $R_4$ are independently from each other H, methyl, or ethyl. Most preferably, R', R" and $R_4$ are H.

As said, n is an integer in the range of 1 to 8. Preferably, n is an integer in the range of 2 to 6. More preferably, n is an integer in the range of 2 to 5. Most preferably, n is 3.

Preferred compounds of general structure (II), as defined above, are selected from the group consisting of but not limited to dimethylaminopropylamine (DMAPA), N,N-diethylaminopropylamine, N,N-dipropylaminopropylamine, N,N-diisopropylaminopropylamine, N,N-dibutylaminopropylamine, N,N-diisobutylaminopropylamine, N,N-dipentylaminopropylamine, N,N-dihexylaminopropylamine, N,N-bis(2-ethylhexyl)aminopropylamine.

DMAPA is particularly preferred.

In a preferred embodiment of the process according to the present invention, $R_3$ in the hydroxyl compound of general formula (III), as detailed above, is often selected from a linear or branched alkyl group having 1 to 30 carbon atoms, more preferably having 1 to 24 carbon atoms, which is optionally substituted by at least one halogen atom, an aryl group, or an aralkyl group. Even more preferably, $R_3$ in the hydroxyl compound of general formula (III) is a linear or branched alkyl group having 1 to 15 carbon atoms, being optionally substituted by at least one halogen atom, an aryl group, or an aralkyl group.

In a more preferred embodiment of the process according to the present invention, $R_3$ in the hydroxyl compound of general formula (III) is a linear or branched alkyl group having 1 to 10 carbon atoms, more preferably having 1 to 6 carbon atoms, being optionally substituted by at least one halogen atom, an aryl group, or an aralkyl group. More preferably, $R_3$ is selected from benzyl, methyl, ethyl, n-propyl, isopropyl, n-butyl, isobutyl, tert-butyl, n-pentyl, isopentyl, hexyl, 2-ethylhexyl or octyl. Most preferably, $R_3$ is an n-propyl group.

Preferred hydroxyl compounds having general formula (III), as detailed above, are selected from the group consisting of but not limited to methanol, ethanol, n-propanol, isopropanol, butanol, isobutanol, tert-butanol, pentanol, isopentanol, hexanol, 2-ethylhexanol and octanol. n-propanol is most preferred.

As said, the oxidative carbonylation reaction of the compound of general structure (II), as detailed above, with the hydroxyl compound of general formula (III), $R_3$—OH (III), as detailed above, is carried out in the presence of a catalyst system, wherein said catalyst system comprises at least one catalyst of the formula $X_kY_l$ [compound $(X_kY_l)$] wherein X is Cu or a metal selected from metals from the Group VIIIB, Y is a halogen, a salt of an organic acid or a salt of an organic compound; and wherein k is an integer 1, 2, 3 or 4 and l is an integer 0, 1, 2, 3 or 4;

at least one halogen containing promoter effective to promote said reaction.

Within the context of the present invention the mention "at least one catalyst of the formula $X_kY_l$ [compound $(X_kY_l)$]" is intended to denote one or more than one compound $(X_kY_l)$. Mixtures of compounds $(X_kY_l)$ can also be used for the purposes of the invention.

In the rest of the text, the expressions "compound $(X_kY_l)$" are understood, for the purposes of the present invention, both in the plural and the singular, that is to say which in the process of the present invention the catalyst system may comprise one or more than one compound $(X_kY_l)$.

Preferably, Y is selected from a group consisting of chlorine, bromine, iodine, formate, acetate, oxalate, acetylacetonate (acac).

According to one embodiment of the process according to the present invention, X in the compound $(X_kY_l)$ is Cu, Y is selected from the group consisting of chlorine, bromine, iodine, formate, acetate, oxalate, acetylacetonate, preferably chlorine, k is 1 and l is an integer 1 or 2. Preferably, the compound $(X_kY_l)$ is CuI, CuCl, $CuCl_2$ or $Cu(OAc)_2$. More preferably, the compound $(X_kY_l)$ is $CuCl_2$.

According to another embodiment of the process according to the present invention, X in the compound $(X_kY_l)$ is a metal selected from metals from the Group VIIIB, preferably X is cobalt, nickel, ruthenium, rhodium, palladium or platinum, Y is selected from the group consisting of chlorine, bromine, iodine, formate, acetate, oxalate, acetylacetonate, preferably chlorine; k is an integer 1, 2, 3 or 4 and l is an integer 0, 1, 2, 3 or 4. Compound $(X_kY_l)$ is preferably selected from the group consisting of $CoC_2$, $CoBr_2$, $CoI_2$, $NiCl_2$, $NiBr_2$, $NiI_2$, $RuCl_3$, $RuBr_3$, $RhCl_3$, $RhBr_3$, $RhI_3$, $PdCl_2$, $PdBr_2$, $PdI_2$, $Pd(OAc)_2$, $Pd(acac)_2$, $PtCl_2$, $PtCl_4$, and combinations thereof. More preferably, compound $(X_kY_l)$ is $PdCl_2$, $Pd(OAc)_2$, $Pd(acac)_2$, $PtCl_2$, $CoCl_2$ and combinations thereof. Most preferably, compound $(X_kY_l)$ is $PdCl_2$.

In another embodiment of the process according to the present invention, the at least one catalyst of the formula $X_kY_l$ [compound $(X_kY_l)$] can be adhered to a carrier material, preferably when l is 0. Non limitative examples of suitable carrier materials may notably include active carbon, graphite, zeolite, alumina or silica.

According to another embodiment of the process according to the present invention, X in the compound $(X_kY_l)$ is Cu, l is equal to 0 and the Cu atoms are applied onto a carrier. Preferably, active carbon or a zeolite is used as carrier.

According to another embodiment of the process according to the present invention, X in the compound $(X_kY_l)$ is a metal selected from metals from the Group VIIIB, preferably X is cobalt, nickel, copper, ruthenium, rhodium, palladium or platinum, l is equal to 0 and the X atoms are applied onto a carrier. Preferably, active carbon or a zeolite is used as carrier.

More preferably, Pd on active carbon (Pd on C) is used.

For the purpose of the invention, the term "promoter" is intended to denote a substance that increases the activity of the compound $(X_kY_l)$, as detailed above.

Within the context of the present invention the mention "at least one halogen containing promoter" is intended to denote one or more than one halogen containing promoter. Mixtures of halogen containing promoters can also be used for the purposes of the invention.

In the rest of the text, the expressions "promoter" are understood, for the purposes of the present invention, both in the plural and the singular, that is to say that in the process of the present invention the catalyst system may comprise one or more than one halogen containing promoter.

In a preferred embodiment of the process according to the present invention, the promoter can be selected from alkali metal halides, earth alkali metal halides, oxo acids of halogen atoms and their salts, complex compounds containing halogen ions, organic halides and halogen molecules, and quaternary ammonium halides, or a mixture thereof. More preferably, the promoter is a compound containing iodine or bromine as halogens or a mixture of these compounds. Most preferably, the halogen containing promoter is NaI, KI, LiI or a combination thereof.

Carbon monoxide suitable for use in the oxidative carbonylation reaction, may be pure gaseous carbon monoxide, or a gaseous mixture wherein carbon monoxide has been diluted with other gaseous substances, such as carbon dioxide, halogens or nitrogen gas, wherein said other gaseous substances preferably have a concentration of at most 10% v/v of the gaseous mixture.

In a preferred embodiment of the process according to the present invention, the oxidizing agent, as used in the oxidative carbonylation reaction, may be pure oxygen ($O_2$), ozone, hydrogen peroxide ($H_2O_2$), a gas containing oxygen such as air or an organic nitro compound or a mixture thereof. Oxygen is preferred.

According to certain embodiments of the process according to the present invention, the oxidative carbonylation reaction is carried out in the presence of other ingredients (Ing) [ingredient (Ing), hereinafter] to improve further the yield and purity of the compound of general structure (I), as detailed above. Typical ingredients (Ing) may include, but are not limited to, ligands, at least one additional inert solvent, organic acids such as notably formic acid, acetic acid, trifluoroacetic acid, inorganic acids such as notably $H_2SO_4$, HCl, $HNO_3$, Lewis acids such as $BF_3$, $AlCl_3$, $FeCl_3$, $FeBr_3$.

According to certain embodiments of the process according to the present invention, the oxidative carbonylation reaction is carried out in the presence of ligands wherein said ligands are selected from the group consisting of a phosphine compound, a phosphite compound, a diamine compound, a triamine compound, a carbene compound or a water soluble compound or mixtures thereof.

Advantageously, said phosphine compound may be selected from the group consisting of triphenylphosphine, 1,2-bis(diphenylphosphino)-ethane, 1,3-bis(diphenylphosphino)propane and tricyclohexylphosphine, 2,2'-Bis(diphenylphosphino)-1,1'-binaphthalene (BINAP), 2,3-O-isopropylidene-2,3-dihydroxy-1,4-bis(diphenylphosphino)butane (DIOP) and mixtures thereof, preferably triphenylphosphine, 1,3-bis(diphenylphosphino) propane and mixtures thereof, and more preferably triphenylphosphine.

Among phosphite compounds mention may be notably made of trimethylphosphite, triethylphosphite, triphenylphosphite, tris(2,4-di-tert-butylphenyl)phosphite, tris(1,1,1,3,3,3-hexafluoro-2-propyl)phosphite and BINAPHOS [—(R)-2-(diphenylphosphino)-1, I'-binaphthalen-2'-yl (S)-1, I'-binaphthalene-2,2'-diyl phosphite].

Among diamine compounds mention may be notably made of ethylenediamine, N,N'-dimethylethylenediamine, 1,2-diaminocyclohexane, 1,2-di(methylamino)cyclohexane, 1,2-diphenylethane-1,2-diamine, and 1,1-Bis(4-methoxyphenyl)-3-methylbutane-1,2-diamine.

Among triamine compounds mention may be notably made of pentamethylethylenetriamine, diethylenetriamine, and N,N,N'-trimethyl-1,4,7-triazacyclononane.

Among carbene ligands mention may be notably made of bis(diisopropylamino)cyclopropenylidene, 1,3-Bis(2,4,6-trimethylphenyl)-4,5-dihydroimidazol-2-ylidene, and 1,4-dimesityl-1,2,3-triazol-5-ylidene Among water soluble ligands mention may be notably made of 2-(diphenylphosphino)-N,N,N-trimethylethanaminium iodide, 1,2-bis[di(m-sodium-sulfonatophenyl)phosphino]ethane (dppets) and 3,3',3"-Phosphanetriyltris(benzenesulfonic acid) trisodium sal (tppts).

Advantageously, the molar ratio of the ligands, in particular the phosphine compound, to the compound $(X_kY_l)$, as described above is from 0.01:1 to 100:1, preferably from 0.01:1 to 50:1, preferably from 0.1:1 to 50:1, more preferably from 0.5:1 to 5:1, even more preferably from 1:1 to 3:1 and most preferably from 1.5:1 to 2.5:1.

In the process according to the invention and in the particular embodiments, it will be clear to the skilled in the art that the amounts of the compounds mentioned here refer to the total amount of said compounds which are used over the entire course of the oxidative carbonylation reaction.

Generally in the process according to the present invention, the oxidative carbonylation reaction is performed at a pressure of at least 1 bar, more preferably at least 5 bar, even more preferably 10 bar, more preferably at least 15 bar, even more preferably at least 20 bar, more preferably at least 25 bar, even more preferably at least 30 bar, and most preferably at least 35 bar. It is further understood that the oxidative carbonylation reaction is generally performed at a pressure of at most 150 bar, more preferably at most 140 bar, even more preferably at most 130 bar, more preferably at most 120 bar, even more preferably at most 100 bar, and most preferably at most 80 bar.

Generally in the process according to the present invention, said oxidative carbonylation reaction is performed at a temperature of at least 90° C., preferably at least 95° C., more preferably at least 100° C., even more preferably at least 105° C., more preferably at least 110° C., even more preferably at least 115° C., and most preferably at least 120° C. It is further understood that said oxidative carbonylation reaction is generally performed at a temperature of at most 200° C., preferably at most 195° C., more preferably at most 190° C., even more preferably at most 185° C., more preferably at most 180° C., even more preferably at most 175° C., and most preferably at most 170° C.

While any order of admixing the compound of general structure (II), the hydroxyl compound of general formula (III), the catalyst system, carbon monoxide, the oxidizing agent, and optionally other ingredients (Ing), as detailed above, can be realized thereby forming the reaction mixture, advantageously, a mixture (M) is first prepared. Said mixture (M) comprises the hydroxyl compound of general formula (III), as detailed above, the catalyst system, as detailed above, and optionally other ingredients (Ing), as detailed above.

Preferably, said mixture (M) consists essentially of the hydroxyl compound of general formula (III), the catalyst system, as detailed above, and optionally other ingredients (Ing), wherein said other ingredients is selected from the group consisting of at least one additional inert solvent, a ligand, an organic acid such as notably formic acid, acetic acid, trifluoroacetic acid, an inorganic acid such as notably $H_2SO_4$, HCl, $HNO_3$, a Lewis acid such as $BF_3$, $AlCl_3$, $FeCl_3$, $FeBr_3$ and mixtures thereof.

The expression "consisting essentially of" is used within the context of the present invention for defining constituents of a reaction mixture which might be comprised in said mixture (M) in minor amounts, without thus modifying the essential properties of the mixture (M).

For the purpose of the present invention, the term "additional inert solvent" refers to a solvent different from the reactants and the products of a given reaction and which is substantially unreactive during the course of the carbonylation reaction. Non limitative examples of suitable inert solvents may notably include aromatic hydrocarbons, in particular benzene, toluene, xylene; nitriles, in particular acetonitrile and benzonitrile; ethers, in particular terahydrofuran and diethylether; esters, in particular ethyl acetate; ketones, in particular acetone and methyl ethyl ketone; amides, in particular N, N-dimethyl formamide and N,N-dimethyl acetamide; pyrrolidones, in particular N-methylpyrrolidone; commercially available solvents, in particular TamiSolve® NxG; ionic liquids, in particular 1-butyl-3-methyl imidazolium chloride, 1-butyl-3-methyl imidazolium bromide, 1-butyl-3-methyl imidazolium iodide, 1-butyl-3-methyl imidazolium tetrafluoroborate, 1-butyl-3-methyl imidazolium dicyanamide, 1-butyl-3-methyl imidazolium tetrachloroaluminate, 1-ethyl-3-methyl imidazolium hexafluorophospate, 1-ethyl-3-methyl imidazolium dicyanaide 1-ethyl-3-methyl imidazolium chloride, N-butyl-4-methyl pyridinium chloride, and combinations thereof.

Preferred inert solvents are toluene, acetonitrile, ethyl acetate, acetone, DMF, NMP, 1-butyl-3-methylimidazolium chloride, 1-ethyl-3-methyl imidazolium dicyanamide.

When the at least one additional inert solvent is present in the mixture (M), then the at least one additional inert solvent is present in the mixture (M) in a weight amount of at least 0.5%, preferably of at least 10%, more preferably at least 20%, even more preferably at least 30%, and even more preferably at least 40%, relative to the total molar amount of all components of mixture (M).

It is further understood that the at least one additional inert solvent is present in the mixture (M) in a weight amount of at most 95%, preferably of at most 90%, more preferably at most 80%, even more preferably at most 70%, and even more preferably at most 60%, relative to the total molar amount of all components of mixture (M).

According to this embodiment, when the at least one additional inert solvent is present in the mixture (M), the compound of general structure (II) is typically added to the mixture (M) in an amount corresponding to a molar ratio of the compound of general structure (II) to the hydroxyl compound of general formula (III) of at least 0.01:1, preferably at least 0.02:1, more preferably at least 0.05:1, even more preferably at least 0.08:1. It is further understood that the molar ratio of the compound of general structure (II) to the hydroxyl compound of general formula (III) in the mixture (M) is generally at most 10:1, preferably at most 5:1, more preferably at most 2:1, even more preferably at most 1.5:1, more preferably at most 1.2:1, and most preferably at most 0.5:1.

According to a particular preferred embodiment, the process according to the invention is carried out in the absence of an additional inert solvent, whereby the hydroxyl compound of general formula (III) functions as a solvent. This being said, the hydroxyl compound of general formula (III) is present in a molar fraction of at least 60%, preferably of at least 70%, more preferably at least 75%, even more preferably at least 82%, more preferably at least 85%, even more preferably at least 88% and most preferably at least 90% relative to the total molar amount of all components of mixture (M). It is further understood that the molar fraction of the hydroxyl compound of general formula (III) in the mixture (M) will generally be at most 99.9%, preferably at most 99%, more preferably at most 98%, even more preferably at most 97%, and most preferably at most 96% relative to the total amount of all components of the mixture (M).

According to this embodiment, in the absence of the at least one additional inert solvent in the mixture (M), the compound of general structure (II) is added to the mixture (M) in an amount corresponding to a molar ratio of the compound of general structure (II) to the hydroxyl compound of general formula (III) in the mixture (M) of at least 0.01:1, preferably at least 0.02:1, more preferably at least 0.05:1. It is further understood that the molar ratio of the compound of general structure (II) to the hydroxyl compound of general formula (III) in the mixture (M) is generally at most 10:1, preferably at most 5:1, more preferably at most 2:1, even more preferably at most 1.0:1, more preferably at most 0.8:1, more preferably at most 0.5:1, and most preferably at most 0.2:1.

Good results can be found when the molar ratio of the compound of general structure (II) to the hydroxyl compound of general formula (III) in the mixture (M) is ranging from 0.05:1 to 0.5:1.

Excellent results can be found when the molar ratio of the compound of general structure (II) to the hydroxyl compound of general formula (III) in the mixture (M) is ranging from 0.05:1 to 0.2:1.

According to one embodiment, the total amount of the compound of general structure (II), as described here above, may be added entirely to said mixture (M) in the beginning of the reaction.

In another embodiment of the process according to the invention, said compound of general structure (II), as described here above, is added intermittently to said mixture (M). Preferably, an interval between subsequent additions of said compound lasts at least 5 minutes, preferably at least 10 minutes, more preferably at least 20 minutes, and most preferably at least 30 minutes. It is further understood that the interval between subsequent additions of said compound generally lasts no more than 80 minutes, preferably no more than 70 minutes, more preferably no more than 60 minutes, and most preferably no more than 50 minutes.

In a particularly preferred embodiment, said compound of general structure (II), as described here above, is added continuously to said mixture (M). Relative to every mole of hydroxyl compound of general formula (III) present in the mixture (M), the compound of general structure (II) is added at an addition rate of at least 0.1 mmole/h, preferably at least 10 mmole/h, more preferably at least 20 mmole/h, even more preferably at least 30 mmole/h, and most preferably at least 40 mmole/h. It is further understood that the compound of general structure (II) is generally added at an addition rate of at most 1000 mmol/h, preferably at most 500 mmole/h, more preferably at most 400 mmole/h, even more preferably at most 250 mmole/h and most preferably at most 150 mmole/h, relative to every mole of hydroxyl compound of general formula (III) present in the mixture (M).

Generally in the process according to the present invention, the molar ratio of the catalyst of the formula $X_kY_l$ [compound $(X_kY_l)$] to the compound of general structure (II) in the mixture (M) is at least 0.00001:1, preferably at least 0.00005:1, preferably at least 0.0001:1, more preferably at least 0.0003:1, even more preferably at least 0.0005:1, and most preferably at least 0.0010:1. It is further understood that the molar ratio of the catalyst of the formula $X_kY_l$ [compound $(X_kY_l)$] to the compound of general structure (II) in the mixture (M) is generally at most 0.5:1, preferably at most 0.1:1, more preferably at most 0.050:1, even more preferably at most 0.040:1.

Good results can be found when the molar ratio of the catalyst of the formula $X_kY_l$ [compound $(X_kY_l)$] to the compound of general structure (II) in the mixture (M) is from 0.0005:1 to 0.040:1.

Generally in the process according to the present invention, the molar ratio of the promoter to the catalyst of the formula $X_kY_l$ [compound $(X_kY_l)$], as detailed above, in the mixture (M) is at least 0.05:1, preferably at least 0.2:1, more preferably at least 1:1 and most preferably at least 5:1. It is further understood that the molar ratio of the promoter to the catalyst of the formula $X_kY_l$ [compound $(X_kY_l)$] in the mixture (M) is generally at most 100:1, preferably at most 80:1, more preferably at most 60:1, and most preferably at most 30:1.

Good results can be found when the molar ratio of the promoter to the catalyst of the formula $X_kY_l$ [compound $(X_kY_l)$] in the mixture (M) is from 0.2:1 to 60:1.

Generally in the process according to the present invention, carbon monoxide is added to the mixture (M) in such a way that the absolute partial pressure of the carbon monoxide used, at room temperature, is at least 0.5 bar, more preferably at least 5 bar, even more preferably 10 bar, more preferably at least 15 bar, even more preferably at least 20 bar, and most preferably at least 25 bar. It is further understood that the absolute partial pressure of the carbon monoxide used, at room temperature, is generally at most 120 bar, even more preferably at most 100 bar, and most preferably at most 80 bar.

Generally in the process according to the present invention, CO is used in a 5-fold, preferably in a 10-fold and more preferably a 15-fold excess relative to the total amount of the compound of general structure (II), as used over the entire course of the oxidative carbonylation reaction, or relative to total amount of the hydroxyl compound of general formula (III), as used over the entire course of the oxidative carbonylation reaction.

According to one embodiment, when the mixture (M) contains less than one equivalent of the compound of general structure (II) for every equivalent of the hydroxyl compound of general formula (III), the amount of CO used is in a in a 5-fold, preferably in a 10-fold and more preferably a 15-fold excess relative to the compound of general structure (II).

According to another embodiment, when the mixture (M) contains less than one equivalent of the hydroxyl compound of general formula (III) for every equivalent of the compound of general structure (II), the amount of CO used is in a 5-fold, preferably in a 10-fold and more preferably a 15-fold excess relative to the hydroxyl compound of general formula (III).

Generally in the process according to the present invention, the oxidizing agent is added to the mixture (M) in such a way that the absolute partial pressure of the oxidizing agent used, at room temperature, is at least 0.5 bar, more preferably at least 3 bar, and even more preferably at least 5 bar. It is further understood that the absolute partial pressure of the oxidizing agent used, at room temperature, is generally at most 60 bar, more preferably at most 40 bar, even more preferably at most 30 bar and most preferably at most 15 bar.

Generally in the process according to the present invention, the oxidizing agent is used in a molar ratio from 0.3:1 to 1.5:1, preferably from 0.5:1 to 1.3:1 relative to total amount of the compound of general structure (II), as used over the entire course of the oxidative carbonylation reaction, or relative to total amount of the hydroxyl compound of general formula (III), as used over the entire course of the oxidative carbonylation reaction.

According to one embodiment, when the mixture (M) contains less than one equivalent of compound of general structure (II) for every equivalent of hydroxyl compound of general formula (III), the amount of the oxidizing agent used is a molar ratio from 0.3:1 to 1.5:1, preferably from 0.5:1 to 1.3:1 relative to the compound of general structure (II).

According to another embodiment, when the mixture (M) contains less than one equivalent of hydroxyl compound of general formula (III) for every equivalent of compound of general structure (II), the amount of the oxidizing agent used is a molar ratio from 0.3:1 to 1.5:1, preferably from 0.5:1 to 1.3:1 relative to the hydroxyl compound of general formula (III).

In an embodiment of the process according to the present invention, the total amount of CO and/or an oxidizing agent, as detailed above, are initially added to said mixture (M). In this embodiment, it is understood that the compound of general structure (II), as described here above, is thus added to the reaction mixture comprising the hydroxyl compound of general formula (III), as described above, the catalyst system, as described above, CO, the oxidizing agent, and optionally other ingredients (Ing), as detailed above.

In another embodiment of the process according to the invention, CO and/or an oxidizing agent as detailed above are added intermittently to said mixture (M). Preferably, an interval between subsequent additions of CO or the oxidizing agent lasts at least 5 minutes, preferably at least 10 minutes, more preferably at least 20 minutes, and most preferably at least 30 minutes. It is further understood that the interval between subsequent additions of CO or the oxidizing agent generally lasts no more than 80 minutes, preferably no more than 70 minutes, more preferably no more than 60 minutes, and most preferably no more than 50 minutes.

In a particularly preferred embodiment of the process according to the present invention, CO and/or an oxidizing agent as detailed above are added continuously to said mixture (M) during the reaction.

Relative to every mole of compound of general structure (II) present in the mixture (M), CO is advantageously added at an addition rate of at least 0.1 mole/h, preferably at least 0.3 mole/h, more preferably at least 0.5 mole/h, even more preferably at least 0.8 mole/h and most preferably at least 1 mole/h. It is further understood that CO is generally added at an addition rate of at most 50 mole/h, preferably at most 45 mole/h, more preferably at most 40 mole/h, and even more preferably at most 30 mole/h, relative to every mole of compound of general structure (II) present in the mixture (M).

Relative to every mole of compound of general structure (II) present in the mixture (M), the oxidizing agent is added at an addition rate of at least 50 mmole/h, preferably of at least 100 mmole/h, and more preferably of at least 250 mmole/h. It is further understood that the oxidizing agent is generally added at an addition rate of at most 10000 mmole/h, preferably of at most 5000 mmole/h, more preferably of at most 3000 mmole/h, even more preferably of at most 2000 mmole/h, and most preferably of at most 1000 mmole/h, relative to every mole of compound of general structure (II) present in the mixture (M).

Generally in the process according to the present invention, said oxidative carbonylation reaction of a compound of general structure (II) with a hydroxyl compound of general formula (III) is carried out in a suitable reactor. The choice of the reactor is not critical, provided that the reactor can enable an efficient contact between compounds that are present in the reactor.

Among suitable reactors mention may be made of a continuous stirred tank reactor, a stirred tank reactor, an autoclave, a plug flow reactor, a fixed bed reactor or a Buss® Loop reactor.

In a preferred embodiment of the process according to the present invention, the pressure in the reactor is kept constant by means of a pressure regulator.

In a particularly preferred embodiment, CO, the oxidizing agent, as detailed above, and the compound of general structure (II) are added continuously to said mixture (M). It is further understood that each component, in particular CO, the oxidizing agent, as detailed above, and the compound of general structure (II), independently of each other, may be continuously added to the mixture (M) with their respective addition rates, as described above. If desired, the reaction volume may be kept constant by continuously removing at least part of the reaction mixture.

According to an alternative embodiment of the present invention, each of the components, in particular, the compound of general structure (II), the hydroxyl compound of general formula (III), the catalyst system, CO, the oxidizing agent, and optionally other ingredients (Ing), as detailed above, are added in a continuous manner, independently of each other, with their respective addition rates, as described above. If desired, the reaction volume may be kept constant by continuously removing at least part of the reaction mixture.

EXAMPLES

The present invention is further illustrated by the examples and comparative examples given below.

Example 1

3330 mmole n-propanol, 2.25 mmole $PdCl_2$ (molar ratio of $PdCl_2$ to DMAPA=0.012:1) and 33 mmole NaI (molar ratio of NaI to PdCl$_2$=14.7:1) were loaded in a 1 liter autoclave. After inertization of the reactor with nitrogen gas, the reactor was heated to a temperature of 125° C. Over the course of 1 h, a total of 195 mmole DMAPA (molar ratio of DMAPA to n-propanol=0.06:1) was added to the reactor at an addition rate of 195 mmole/h (0.060 mole/h relative to every mole of n-propanol). CO was introduced into the reactor at an addition rate of 2.95 mole/h (15.13 mole/h relative to every mole of DMAPA) while O$_2$ was introduced into the reactor at an addition rate of 134 mmole/h (0.69 mole/h relative to every mole of DMAPA), thereby using a back pressure regulator for keeping the total pressure in the reactor at a constant level of 40 bar. The data are summarized in Table 1.

Example 2

3330 mmole n-propanol, 1.1 mmole PdCl$_2$ (molar ratio of PdCl$_2$ to DMAPA=0.003:1) and 16.7 mmole NaI (molar ratio of NaI to PdCl$_2$=15.2:1) were loaded in a 1 liter autoclave. After inertization of the reactor with nitrogen gas, the reactor was heated to a temperature of 125° C. Over the course of 2 h, a total of 390 mmole DMAPA (molar ratio of DMAPA to n-propanol=0.12:1) was added to the reactor at an addition rate of 195 mmole/h (0.060 mole/h relative to every mole of n-propanol). CO and O$_2$ were introduced into the reactor at an addition rate of 2.95 mole/h (7.56 mole/h relative to every mole of DMAPA) and 134 mmole/h (0.34 mole/h relative to every mole of DMAPA) respectively, thereby using a back pressure regulator for keeping the total pressure in the reactor at a constant level of 40 bar. The data are summarized in Table 1.

Example 3

3330 mmole n-propanol, 1.1 mmole PdCl$_2$ (molar ratio of PdCl$_2$ to DMAPA=0.003:1) and 16.7 mmole NaI (molar ratio of NaI to PdCl$_2$=15.2:1) were loaded in a 1 liter autoclave. After inertization of the reactor with nitrogen gas, the reactor was heated to a temperature of 125° C. Over the course of 2 h, a total of 390 mmole DMAPA (molar ratio of DMAPA to n-propanol=0.12:1) was added to the reactor at an addition rate of 195 mmole/h (0.060 mole/h relative to every mole of n-propanol). CO and O$_2$ were introduced into the reactor at an addition rate of 4.91 mole/h (12.59 mole/h relative to every mole of DMAPA) and 223 mmole/h (0.57 mole/h relative to every mole of DMAPA) respectively, thereby using a back pressure regulator for keeping the total pressure in the reactor at a constant level of 40 bar. The data are summarized in Table 1.

Example 4

3330 mmole n-propanol, 1.1 mmole PdCl$_2$ (molar ratio of PdCl$_2$ to DMAPA=0.006:1) and 16.7 mmole NaI (molar ratio of NaI to PdCl$_2$=15.2:1) were loaded in a 1 liter autoclave. After inertization of the reactor with nitrogen gas, the reactor was heated to a temperature of 125° C. CO was introduced into the reactor at an addition rate of 2.95 mole/h (15.13 mole/h relative to every mole of DMAPA) while O$_2$ was introduced into the reactor at an addition rate of 134 mmole/h (0.69 mole/h relative to every mole of DMAPA), thereby using a back pressure regulator for keeping the total pressure in the reactor at a constant level of 40 bar. Over the course of 1 h, 195 mmole DMAPA (molar ratio of DMAPA to n-propanol=0.06:1) was added to the reactor at an addition rate of 195 mmole/h (0.060 mole/h relative to every mole of n-propanol). The data are summarized in Table 1.

Example 5

3330 mmole n-propanol, 2750 mmole DMF (45% relative to the total molar amount of all components of mixture M), 1.1 mmole PdCl$_2$ (molar ratio of PdCl$_2$ to DMAPA=0.003:1) and 16.7 mmole NaI (molar ratio of NaI to PdCl$_2$=15.2:1) were loaded in a 1 liter autoclave. After inertization of the reactor with nitrogen gas, the reactor was heated to a temperature of 125° C. CO was introduced into the reactor at an addition rate of 2.95 mole/h (7.56 mole/h relative to every mole of DMAPA) while O$_2$ was introduced into the reactor at an addition rate of 134 mmole/h (0.34 mole/h relative to every mole of DMAPA), thereby using a back pressure regulator for keeping the total pressure in the reactor at a constant level of 40 bar. Over the course of 2 h, a total of 390 mmole DMAPA (molar ratio of DMAPA to n-propanol=0.12:1) was added to the reactor at an addition rate of 195 mmole/h (0.060 mole/h relative to every mole of n-propanol). The data are summarized in Table 1.

Example 6

3330 mmole n-propanol, 390 mmole DMAPA (molar ratio of DMAPA to n-propanol=0.12:1), 14 mmole PdCl$_2$ (molar ratio of PdCl$_2$ to DMAPA=0.036:1) and 3 mmole NaI (molar ratio of NaI to PdCl$_2$=0.2:1) were loaded in a 1 liter autoclave. After inertization of the reactor with nitrogen gas, CO and O$_2$ were loaded. The initial partial pressure of CO was 50 bar, the initial partial pressure of 02 was 6 bar. Subsequently, the reaction mixture was heated to 165° C. The data are summarized in Table 1.

Example 7

3330 mmole n-propanol, 1.1 mmole PdCl$_2$ (molar ratio of PdCl$_2$ to DMAPA=0.003:1) and 15 mmole KI (molar ratio of KI to PdCl$_2$=13.6:1) were loaded in a 1 liter autoclave. After inertization of the reactor with nitrogen gas, the reactor was heated to a temperature of 125° C. CO was introduced into the reactor at an addition rate of 2.95 mole/h (7.56 mole/h relative to every mole of DMAPA) while O$_2$ was introduced into the reactor at an addition rate of 134 mmole/h (0.34 mole/h relative to every mole of DMAPA), thereby using a back pressure regulator for keeping the total pressure in the reactor at a constant level of 40 bar. A total of 390 mmole DMAPA (molar ratio of DMAPA to n-propanol=0.12:1) was added to the reactor at an addition rate of 195 mmole/h (0.060 mole/h relative to every mole of n-propanol) over the course of two hours. The data are summarized in Table 1.

It was found that the combination of the promoter NaI with the catalyst resulted in slightly higher propamocarb yields than when KI was used as a promoter.

Example 8

3330 mmole n-propanol, 1.1 mmole PdCl$_2$ (molar ratio of PdCl$_2$ to DMAPA=0.006:1) and 16.7 mmole NaI (molar ratio of NaI to PdCl$_2$=15.2:1) were loaded in a 1 liter autoclave. After inertization of the reactor with nitrogen gas, CO and O$_2$ were loaded. The initial partial pressure of CO was 60 bar, the initial partial pressure of O$_2$ was 7 bar. Subsequently, the reaction mixture was heated to 125° C. 195 mmole DMAPA (molar ratio of DMAPA to n-propanol=0.06:1) was added to the reactor at an addition rate of 195 mmole/h (0.060 mole/h relative to every mole of n-propanol) for 60 min. The data are summarized in Table 1.

Example 9

An oxidative carbonylation reaction was performed under the same conditions as in Example 2. 2.3 mmole of triphenylphosphine (molar ratio of triphenylphosphine to $PdCl_2$=2.1:1) was added to the reactor. The data are summarized in Table 1.

Example 10

3330 mmole n-propanol, 1.1 mmole $PdCl_2$ (molar ratio of $PdCl_2$ to DMAPA=0.006:1) and 16.7 mmole NaI (molar ratio of NaI to $PdCl_2$=15.2:1) were loaded in a 1 liter autoclave. After inertization of the reactor with nitrogen gas, CO and $O_2$ were loaded. The initial partial pressure of CO was 50 bar, the initial partial pressure of $O_2$ was 6 bar. Subsequently, the reaction mixture was heated to 165° C. 195 mmole DMAPA (molar ratio of DMAPA to n-propanol=0.06:1) was added to the reactor at an addition rate of 390 mmole/h (0.12 mole/h relative to every mole of n-propanol) for 30 min. The data are summarized in Table 1.

Comparative Example 1

3330 mmole n-propanol, 1.1 mmole $PdCl_2$ (molar ratio of $PdCl_2$ to n-butylamine=0.003:1) and 16.7 mmole NaI (molar ratio of NaI to $PdCl_2$=15.2:1) were loaded in a 1 liter autoclave. After inertization of the reactor with nitrogen gas, CO and $O_2$ were loaded. The initial partial pressure of CO was 60 bar, the initial partial pressure of $O_2$ was 7 bar. Subsequently, the reaction mixture was heated to 165° C. 410 mmole n-butylamine (molar ratio of n-butylamine to n-propanol=0.12:1) was added to the reactor at an addition rate of 410 mmole/h for 1 h (0.12 mole/h relative to every mole of n-propanol). A low but gradually increasing product yield was found. The data are summarized in Table 1.

This example shows that simple primary mono-amines can be amidated under the conditions of the present invention, however, at a somewhat lower rate and selectivity.

Comparative Example 2

3330 mmole n-propanol, 1.1 mmole $PdCl_2$ (molar ratio of $PdCl_2$ to n-butylamine=0.003:1) and 16.7 mmole NaI (molar ratio of NaI to $PdCl_2$=15.2:1) were loaded in a 1 liter autoclave. After inertization of the reactor with nitrogen gas, CO and $O_2$ were loaded. The initial partial pressure of CO was 55 bar, the initial partial pressure of $O_2$ was 6.5 bar. Subsequently, the reaction mixture was heated to 165° C. A mixture of n-butylamine and triethylamine (molar ratio of triethylamine to n-butylamine=1:1) was added to the reactor at an addition rate of 820 mmole/h for 1 h (molar ratio of n-butylamine to n-propanol=0.12:1, molar ratio of triethylamine to n-propanol=0.12:1).

It was found that the product yield stagnates at a certain level and that both n-butylamine and triethylamine start to accumulate. The data are summarized in Table 1.

Comparison of the results of Comparative Example 1 and Comparative Example 2 show that the addition of a tertiary amine significantly reduces the conversion and selectivity of the oxidative carbonylation of the primary amine.

It was surprisingly found, that the process according to the present invention, provides superior results when the substrates contain both a primary and tertiary amine functionality in one molecule (i.e. a compound of general structure (II)), in particular DMAPA.

Comparative Example 3

3330 mmole n-propanol and 1.1 mmole $PdCl_2$ (molar ratio of $PdCl_2$ to DMAPA=0.006:1) were loaded in a 1 liter autoclave. After inertization of the reactor with nitrogen gas, CO and $O_2$ were loaded. The initial partial pressure of CO was 50 bar, the initial partial pressure of $O_2$ was 6 bar. Subsequently, the reaction mixture was heated to 165° C. 195 mmole DMAPA (molar ratio DMAPA to n-propanol=0.06:1) was added to the reactor at an addition rate of 195 mmole/h (0.060 mole/h relative to every mole of n-propanol) for 60 min. The data are summarized in Table 1.

This example clearly underlines the necessity of a promoter for the oxidative carbonylation reaction to proceed.

TABLE 1

| | Ex. 1 | Ex. 2 | Ex. 3 | Ex. 4 | Ex. 5 | Ex. 6 | Ex. 7 | Ex 8 | Ex. 9 | Ex. 10 | Comp. Ex. 1 | Comp. Ex. 2 | Comp. Ex. 3 |
|---|---|---|---|---|---|---|---|---|---|---|---|---|---|
| Reaction Temperature (° C.) | 125 | 125 | 125 | 125 | 125 | 165 | 125 | 125 | 125 | 165 | 165 | 165 | 165 |
| $CO/O_2$ pressure (bar) | 40 | 40 | 40 | 40 | 40 | | 40 | | 40 | | | | |
| CO initial partial pressure (bar) | | | | | | 70 | | 60 | | 50 | 60 | 55 | 50 |
| $O_2$ initial partial pressure (bar) | | | | | | 8 | | 7 | | 6 | 7 | 6.5 | 6 |
| Hydroxyl compound (III) | | | | | | | | | | | | | |
| n-propanol (mmole) | 3330 | 3330 | 3330 | 3330 | 3330 | 3330 | 3330 | 3330 | 3330 | 3330 | 3330 | 3330 | 3330 |
| Catalyst ($X_kY_l$) | | | | | | | | | | | | | |
| $PdCl_2$ (molar ratio to II) | 0.012:1 | 0.003:1 | 0.003:1 | 0.006:1 | 0.003:1 | 0.036:1 | 0.003:1 | 0.006:1 | 0.003:1 | 0.006:1 | 0.003:1 | 0.003:1 | 0.006:1 |
| Promoter | | | | | | | | | | | | | |
| NaI (molar ratio to $X_kY_l$) | 14.7:1 | 15.2:1 | 15.2:1 | 15.2:1 | 15.2:1 | 0.2:1 | | 15.2:1 | 15.2:1 | 15.2:1 | 15.2:1 | 15.2:1 | |
| KI (molar ratio to $X_kY_l$) | | | | | | | 13.6:1 | | | | | | |
| Solvent | | | | | | | | | | | | | |
| DMF (molar amount of M) | | | | | 45% | | | | | | | | |
| Mixture (M) (mmole) | 3365.2 | 3347.8 | 3347.8 | 3347.8 | 6097.8 | 3347.0 | 3346.1 | 3347.8 | 3347.8 | 3347.8 | 3347.8 | 3347.8 | 3331.1 |

TABLE 1-continued

| | Ex. 1 | Ex. 2 | Ex. 3 | Ex. 4 | Ex. 5 | Ex. 6 | Ex. 7 | Ex 8 | Ex. 9 | Ex. 10 | Comp. Ex. 1 | Comp. Ex. 2 | Comp. Ex. 3 |
|---|---|---|---|---|---|---|---|---|---|---|---|---|---|
| Amine compound (II) | | | | | | | | | | | | | |
| DMAPA (molar ratio to III) | 0.06:1 | 0.12:1 | 0.12:1 | 0.06:1 | 0.12:1 | 0.12:1 | 0.12:1 | 0.06:1 | 0.12:1 | 0.06:1 | | | 0.06:1 |
| n-butylamine (molar ratio to III) | | | | | | | | | | | 0.12:1 | 0.12:1 | |
| triethylamine (molar ratio to III) | | | | | | | | | | | | 0.12:1 | |
| Ingredients (Ing) | | | | | | | | | | | | | |
| Triphenylphosphine (molar ratio to $X_kY_l$) | | | | | | | | | 2.1:1 | | | | |
| CO (mole/h relative to 1 mole II) | 15.13 | 7.56 | 12.59 | 15.13 | 7.56 | | 7.56 | | 7.56 | | | | |
| Oxidizing agent | | | | | | | | | | | | | |
| $O_2$ (mole/h relative to 1 mole II) | 0.69 | 0.34 | 0.57 | 0.69 | 0.34 | | 0.34 | | 0.34 | | | | |
| PRODUCT YIELD (%) | 95.7 | 82.5 | 80 | 93.4 | 75.6 | 61.1 | 77.2 | 83.7 | 86 | 73 | 22 | 8 | <1% |
| Ureum | 0 | 3.1 | 1.0 | 1.8 | 5.7 | na | 1.4 | 1.5 | 3.4 | 8.5 | 33 | 66 | <0.5% |

The invention claimed is:

1. A process for the preparation of a compound of general structure (I)

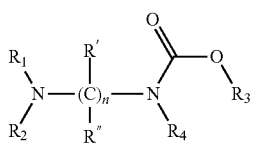

wherein
each of R1 and R2, are equal to or different from each other, and are independently selected from an alkyl group having 1 to 10 carbon atoms, which is optionally substituted by at least one of (1) a halogen atom; (2) an aryl group; or (3) an aralkyl group;
R3 is selected from an alkyl group having 1 to 36 carbon atoms, which is optionally substituted by at least one of (1) a halogen atom; (2) an aryl group; or (3) an aralkyl group;
each of R', R" and R4, are equal to or different from each other, and are independently selected from H and an alkyl group having 1 to 10 carbon atoms, which is optionally substituted by at least one of (1) a halogen atom; (2) an aryl group; or (3) an aralkyl group;
n is an integer in the range from 1 to 8,
which process comprises an oxidative carbonylation reaction of a compound of general structure (II)

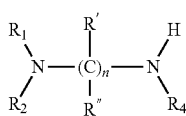

wherein R1, R2, R4, R', R" and n have the same meaning as defined here above, with a hydroxyl compound of general formula (III),

R3-OH            (III), wherein R3 has the same meaning as defined here above, and in the presence of a catalyst system, wherein said catalyst system comprises
at least one catalyst of the compound $(X_kY_l)$ wherein X is Cu or a metal selected from metals from the Group VIIIB, Y is a halogen, an anion of an organic acid or an anion of an organic compound; and wherein k is an integer 1, 2, 3 or 4 and l is an integer 0, 1, 2, 3 or 4; and
at least one halogen containing promoter effective to promote said reaction.

2. The process according to claim 1, wherein X in the compound $(X_kY_l)$ is Cu, Y is selected from the group consisting of chlorine, bromine, iodine, formate, acetate, oxalate, and acetylacetonate; k is 1 and l is an integer of 1 or 2 or X in the compound $(X_kY_l)$ is cobalt, nickel, ruthenium, rhodium, palladium or platinum, Y is selected from the group consisting of chlorine, bromine, iodine, formate, acetate, oxalate, and acetylacetonate; k is an integer of 1, 2, 3 or 4 and l is an integer of 0, 1, 2, 3 or 4.

3. The process according to claim 1, wherein the oxidative carbonylation reaction is carried out with a carbon monoxide compound and an oxidizing agent wherein said carbon monoxide compound is pure gaseous carbon monoxide or a gaseous mixture comprising carbon monoxide diluted with other gaseous substances selected from the group consisting of carbon dioxide, halogens and nitrogen gas and wherein said oxidizing agent is selected from the group consisting of pure oxygen ($O_2$), ozone, hydrogen peroxide ($H_2O_2$) and a gas containing oxygen.

4. The process according to claim 1, wherein the oxidative carbonylation reaction is carried out in the presence of other ingredients (Ing) comprising a ligand, at least one additional inert solvent, an organic acid, an inorganic acid or a Lewis acid.

5. The process according to claim 4, wherein the ingredient (Ing) comprises a ligand wherein said ligand is selected from the group consisting of a phosphine compound, a phosphite compound, a diamine compound, a triamine compound, a carbene compound, a water soluble compound and mixtures thereof.

6. The process according to claim 1, wherein the oxidative carbonylation reaction is performed at a pressure of at least 1 bar and at a pressure of at most 150 bar and at a temperature of at least 90° C. and at a temperature of at most 200° C.

7. The process according to claim 1, wherein a mixture (M) is first prepared by admixing the hydroxyl compound of general formula R3-OH (III), wherein R3 has the same meaning as defined above, with the catalyst system as defined above.

8. The process according to claim 7, wherein the mixture (M) comprises the hydroxyl compound of general formula R3-OH (III), wherein R3 has the same meaning as defined above, the catalyst system, as defined above, and at least one additional inert solvent wherein said additional inert solvent comprises aromatic hydrocarbons, nitriles, ethers, esters, ketones, amides, pyrrolidones or ionic liquids.

9. The process according to claim 8, wherein the compound of general structure (II) is added to the mixture (M) in an amount corresponding to a molar ratio of the compound of general structure (II) to the hydroxyl compound of general formula (III) of at least 0.05:1, and the molar ratio of the compound of general structure (II) to the hydroxyl compound of general formula (III) in the mixture (M) is at most 1.2:1.

10. The process according to claim 7, wherein the process is carried out in the absence of an additional inert solvent and wherein the hydroxyl compound of general formula (III) functions as a solvent.

11. The process according to claim 10, wherein the compound of general structure (II) is added to the mixture (M) in an amount corresponding to a molar ratio of the compound of general structure (II) to the hydroxyl compound of general formula (III) in the mixture (M) of at least 0.01:1 and the molar ratio of the compound of general structure (II) to the hydroxyl compound of general formula (III) in the mixture (M) is at most 0.5:1.

12. The process according to claim 7, wherein the compound of general structure (II) is added intermittently to the mixture (M) or the compound of general structure (II) is added continuously to the mixture (M).

13. The process according to claim 12, wherein the compound of general structure (II) is added continuously to the mixture (M) at an addition rate of at least 30 mmole/h, and the compound of general structure (II) is added continuously to the mixture (M) at an addition rate of at most 250 mmole/h, relative to every mole of hydroxyl compound of general formula (III) present in the mixture (M).

14. The process according to any claim 12, wherein the molar ratio of the catalyst of compound $(X_kY_l)$ to the compound of general structure (II) in the mixture (M) is at least 0.00001:1 and the molar ratio of the catalyst of compound $(X_kY_l)$ to the compound of general structure (II) in the mixture (M) is at most 0.5:1.

15. The process according to claim 12, wherein a carbon monoxide compound and/or an oxidizing agent are added intermittently to the mixture (M) or a carbon monoxide compound and/or an oxidizing agent are added continuously to the mixture (M) during the reaction, wherein carbon monoxide compound means pure gaseous carbon monoxide or a gaseous mixture comprising carbon monoxide diluted with other gaseous substances.

16. The process according to claim 15, wherein the carbon monoxide compound is added continuously to the mixture (M) during the reaction and at an addition rate, relative to every mole of compound of general structure (II) present in the mixture (M), of at least 0.8 mole CO/h and at an addition rate, relative to every mole of compound of general structure (II) present in the mixture (M), of at most 50 mole CO/h, and the oxidizing agent is added continuously to the mixture (M) during the reaction and at an addition rate, relative to every mole of compound of general structure (II) present in the mixture (M), of at least 100 mmole/h, and at an addition rate, relative to every mole of compound of general structure (II) present in the mixture (M), of at most mmole 2000 mmole/h.

* * * * *